(12) United States Patent
Sijben et al.

(10) Patent No.: US 8,188,309 B2
(45) Date of Patent: May 29, 2012

(54) PROCESS FOR PREPARING AROMATIC CARBOXYLIC ACIDS

(75) Inventors: Johannes Maria Franciscus Sijben, Etten-Leur (NL); Herman Jozef Claudius De Meyer, Brasschaat (BE)

(73) Assignee: Process Design Center B.V., Breda (NL)

( * ) Notice: Subject to any disclaimer, the term of this patent is extended or adjusted under 35 U.S.C. 154(b) by 697 days.

(21) Appl. No.: 11/793,624

(22) PCT Filed: Dec. 20, 2005

(86) PCT No.: PCT/NL2005/000877
§ 371 (c)(1),
(2), (4) Date: Mar. 27, 2008

(87) PCT Pub. No.: WO2006/068472
PCT Pub. Date: Jun. 29, 2006

(65) Prior Publication Data
US 2009/0062563 A1 Mar. 5, 2009

Related U.S. Application Data

(60) Provisional application No. 60/638,021, filed on Dec. 20, 2004, provisional application No. 60/654,986, filed on Feb. 22, 2005.

(51) Int. Cl.
*C07C 51/16* (2006.01)
(52) U.S. Cl. ........ 562/412; 562/405; 562/407; 562/408; 562/409; 562/416
(58) Field of Classification Search .................. None
See application file for complete search history.

(56) References Cited

U.S. PATENT DOCUMENTS

| | | | |
|---|---|---|---|
| 5,371,283 A * | 12/1994 | Kingsley et al. | 562/416 |
| 6,034,269 A | 3/2000 | Turner et al. | |
| 6,649,791 B2 | 11/2003 | Srinivas et al. | |
| 2002/0028968 A1 * | 3/2002 | Graham et al. | 562/415 |
| 2003/0008770 A1 | 1/2003 | Srinivas et al. | |
| 2005/0192459 A1 * | 9/2005 | Metelski et al. | 562/416 |

FOREIGN PATENT DOCUMENTS

| | | |
|---|---|---|
| EP | 0 041 784 | 12/1981 |
| WO | WO 98/38150 | 9/1998 |

OTHER PUBLICATIONS

Chavan, S. et al. "A novel zeolite-encapsulated $\mu_3$-oxo Co/Mn cluster catalyst for oxidation of *para*-xylene to terephthalic acid." *Chemical Communications*, vol. 12, 2001, pp. 1124-1125.
Chavan S. et al. "Selective oxidation of *para*-Xylene to Terephthalic Acid by $\mu_3$-Oxo-Bridged Co/Mn Cluster Complexes Encapsulated in Zeolite-Y." *Journal of Catalysts*, vol. 204, 2001, pp. 409-419.
Chisem, I. et al. "Catalytic oxidation of alkyl aromatics using a novel silica supported Schiff base complex." Chemical Communications, vol. 18, 1998, pp. 1949-1950.

* cited by examiner

*Primary Examiner* — Sudhakar Katakam
(74) *Attorney, Agent, or Firm* — Weingarten, Schurgin, Gagnebin & Lebovici LLP

(57) ABSTRACT

The present invention relates to a process for making terephthalic acid by reacting a starting material and oxygen in the presence of a heterogeneous catalyst and p-xylene as solvent to produce a solution of terephthalic acid (TPA). The starting material is p-xylene, p-toluic acid, 4 carboxybenzaldehyde, or a mixture of any two or more thereof. No solid TPA is formed during the reaction in contrast to previous manufacturing methods that utilize acidic solvents and precipitate TPA as it forms. By avoiding the direct precipitation of TPA during formation, the present methods avoid many shortcomings of the conventional manufacturing methods used to produce TPA. In particular, the present methods do not require additional purification steps to remove reaction byproducts; film grade TPA can be obtained directly from starting material in a one-step process.

23 Claims, 4 Drawing Sheets

PROCESS FOR PREPARING AROMATIC CARBOXYLIC ACIDS

This application is a §371 national phase filing of PCT/NL2005/000877 filed Dec. 20, 2005; and claims priority to U.S. application 60/638,021 filed Dec. 20, 2004, and to U.S. application 60/654,986 filed Feb. 22, 2005.

FIELD OF THE INVENTION

This invention relates to processes for manufacturing terephthalic acid, particularly processes using a heterogeneous catalyst. The invention further relates to processes for manufacturing film-grade terephthalic acid.

BACKGROUND

Terephthalic acid (TPA) is an aromatic carboxylic acid widely used as a chemical intermediate. Terephthalic acid is of commercial interest to the polymer industry because of its use in the manufacture of saturated polyesters, such as polyethylene terephthalate (PET), and its copolymers. Worldwide production of TPA and its corresponding dimethyl ester (dimethyl terephthalate) ranked about $25^{th}$ in tonnage of all chemicals produced in 1992, and about $10^{th}$ among all organic chemicals.

As shown in the scheme below, the oxidation of p-xylene by molecular oxygen is a radical initiated, step-wise reaction which produces two main intermediates, p-toluic acid and 4-formyl-benzoic acid (also known as 4-carboxybenzaldehyde or 4-CBA).

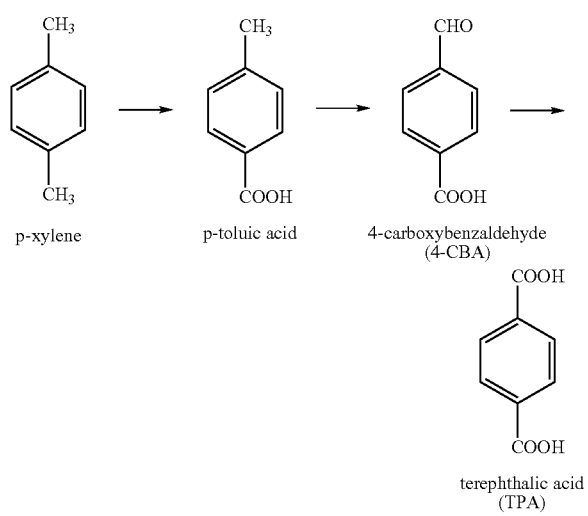

There are numerous process methods available for manufacturing TPA, each of which have varying production and purity yields for TPA. Most of these processes involve oxidation of p-xylene with an oxygen source, e.g., air or $O_2$ gas, in the presence of liquid phase homogeneous catalysts containing at least cobalt and/or manganese metals. In addition, most of these processes are conducted in the presence of an acidic solvent, such as acetic acid. The acetic acid tends to oxidize, leading to solvent loss, and must be separated from water at the end of the process; recovery of acetic acid is therefore very expensive. Conventional processes also employ corrosive bromine promoters as a radical source, e.g. HBr, NaBr, or other metal bromines. Consequently, these processes are typically conducted in expensive, titanium-clad reactors. As it is formed, the TPA precipitates from the acetic acid reaction medium, resulting in a concentrated slurry of TPA particles.

The TPA precipitate is typically contaminated with 4-CBA due to incomplete oxidation during the reaction. Contamination with 4-CBA can be substantial; for instance, some production processes yield a TPA stock which has approximately 5000 ppm of 4-CBA (Pernicona et al., Catalysis Today, Vol. 44: p. 129-135 (1998)). The presence of even minor amounts of 4-CBA in the terephthalic acid interferes with high-grade polyester synthesis such as the polycondensation of TPA to PET. Hence, the 4-CBA must be removed from the TPA. However, removal of 4-CBA is complicated by the fact that it readily co-crystallizes with TPA. Typically, the TPA is purified by high-pressure hydrogenation of the aldehyde to the easily separable p-toluic acid as described in U.S. Pat. No. 5,200,557. However, this additional step and the subsequent recrystallization that accompanies it are expensive.

Currently, there exists a need for methods of synthesizing terephthalic acid with sufficiently high yields and suitable purity for subsequent high-grade manufacturing processes, so as to avoid the use of additional purification steps. In addition, there exists a need for methods that avoid the use of corrosive feed materials or other process materials which may be harmful to the environment, such as NaBr or HBr.

It has been described in WO-A 98/38150 to produce terephthalic acid in such a way that substantially all of the aromatic carboxylic acid produced in the course of the reaction is maintained in solution during the reaction. No specific measures have been described for maintaining the acid in solution.

SUMMARY OF THE INVENTION

In one aspect, the invention relates to methods for manufacturing terephthalic acid that include reacting a starting material and oxygen in the presence of a heterogeneous catalyst and p-xylene as solvent to produce a solution of terephthalic acid. More specifically the invention concerns a method comprising reacting a starting material and oxygen in the presence of a heterogeneous catalyst and p-xylene as solvent to produce a solution of terephthalic acid without formation of solid terephthalic acid during the reaction, wherein the starting material is p-xylene, p-toluic acid, 4-carboxybenzaldehyde, or a mixture of two or more thereof.

P-xylene is used as the starting material. No solid terephthalic acid is formed during the reaction. The concentration of TPA in solution can be at least 0.5, 1, or 2 weight percent (wt %) or more and can range up to 5 or 10 wt % or greater than 10 wt %. Because the methods of the present invention avoid direct precipitation of terephthalic acid as it is formed, the methods avoid many of the shortcomings of conventional processes.

The reaction conditions are maintained such that the reaction products are in the liquid phase, thereby reducing the 4-CBA content in TPA after crystallization. Typically the processes do not require further purification to produce film grade TPA. As a result, compared to the current technology, inventive methods generally require 10 to 50% less energy per metric ton of TPA produced.

The heterogeneous catalyst used in inventive methods is a catalyst that exists in a different phase than that of the solution containing reactants and the terephthalic acid product. The heterogeneous catalyst is present as a solid catalyst. For example, the solid catalyst can be immobilized on a substrate such as a fixed bed or can be a slurry catalyst. Any suitable solid catalyst may be used such as those including zeolites or a mesoporous encapsulating matrix such as mesoporous $SiO_2$ or β-SiC, carbon or carbon nanotubes, and a catalytic principle such as cobalt-manganese compounds. In some embodiments, the starting material and oxygen are reacted in the presence of the catalyst and a halogen-containing agent, including but not limited to aryl halides. Suitable aryl halides include aryl bromides such as 9-bromoanthracene, 9,10-dibromoanthracene, mixtures thereof, and the like.

The solvent for use with the present invention is p-xylene, optionally in the further presence of water as co-solvent. The ratio of water to p-xylene in the solvent typically is such that with the temperature and pressure used during the reaction one homogeneous liquid phase is maintained. Preferably this ratio ranges from about 0.01 to about 1, as measured by weight. In a mixture of water and p-xylene the concentration of terephthalic acid in the terephthalic acid solution generally ranges from about 0.5 wt % to about 5 wt %, although higher or lower values are possible.

The reaction medium typically includes oxygen, p-xylene, water and terephthalic acid as a single homogeneous liquid phase.

The present methods may be carried out as a batch process or as a continuous process. A single reactor or two or more reactors may be used. When multiple reactors are employed, they can be arranged in series, parallel, or a combination thereof. As will be understood by those of skill in the art, the mixing pattern in each reactor can be adjusted for the specific application and is independently backmixed, partially backmixed, or not backmixed. One or more reactors can be operated adiabatically, non-adiabatically, isothermally, or non-isothermally. Typically, the one or more reactors are operated adiabatically or non-adiabatically with boiling cooling.

The oxygen and p-xylene used in the reaction may be supplied to the reaction by any suitable methods known to those of skill in the art. The oxygen can be supplied from an external source or generated in situ. It may be supplied from a gas comprising at least 18% oxygen by volume, e.g., as air, but higher or lower concentrations of oxygen can be used. For example, the oxygen can be supplied at a concentration of at least 90% by volume. When the reaction is carried out in one or more reactors, the oxygen is supplied to the one or more reactors dissolved in one or more liquid reactor feeds. Two or more reactors can also be simultaneously supplied with oxygen from an oxygen feed. Likewise, two or more reactors can be simultaneously supplied with p-xylene from p-xylene feeds.

The present methods of producing TPA are typically carried out at elevated temperatures and pressures. In some embodiments the reaction of p-xylene and oxygen is carried out at temperature of about 150° C. to about 400° C., and in others from about 200° C. to about 300° C. The reaction can be carried out at a pressure of from about 5 bar to about 80 bar, and particularly at about 30 bar to about 50 bar.

Terephthalic acid can be separated from the solution of terephthalic acid by any suitable method known to those skilled in the art. The separation may be carried out by precipitation, crystallization, or both precipitation and crystallization of the terephthalic acid from the reaction solution. A particularly useful method for carrying out the separation is by flash evaporation of water from the solution of terephthalic acid. It will be understood by those of skill in the art that flash evaporation (e.g., pressure flashing) of water will cause at least some portion p-xylene present to vaporize as well. Water may be separated from the reaction mixture or the TPA solution before, during or after the separation of TPA itself. Typically, the water is separated by pressure flashing, subsequent liquid-liquid separation of the condensed vapors, and recycling of the organic phase. At least a portion of the water separated can be recycled for use as co-solvent. The separated TPA is typically film-grade terephthalic acid, though the invention is not so limited.

DETAILED DESCRIPTION

Figure 1:
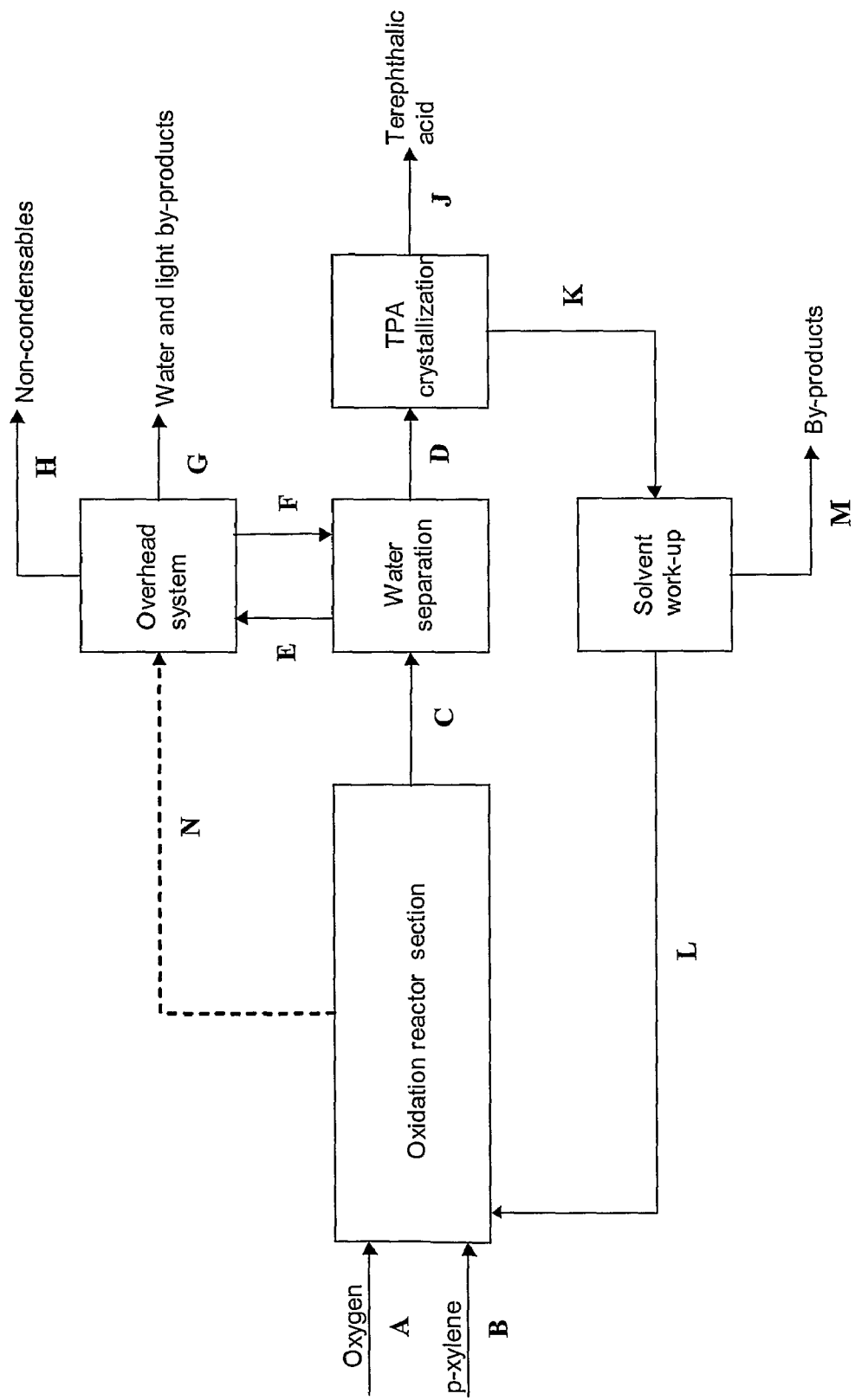
FIG. 1 shows a schematic block flow sheet illustrating one embodiment of the present invention.

The present invention relates to processes for manufacturing TPA, including film grade TPA, using heterogeneous catalysis, e.g., a solid catalyst, in a way that prevents any precipitation of TPA during the reaction. A block flow sheet of one embodiment of the present invention is shown in FIG. 1. An oxygen feed (A), a p-xylene feed (B) and a solvent stream (L) are fed into a reaction section including one or more continuous oxidation reactors in a series or parallel arrangement. Reactors containing fluidized beds with intrinsic recycle of catalyst, fixed beds with static arrangement of catalyst, or cross flow beds and membrane reactors may also be used. The concentration of oxygen in the oxygen feed ranges from 1% to 100% by volume, and is typically at least 18%, at least 80%, at least 85%, at least 90%, at least 95%, or even at least 98 or 99% by volume. The oxygen feed can be supplied to only one reactor, or simultaneously to several reactors in any ratio. The p-xylene feed comprises p-xylene at least in part, but any p-xylene concentration up to 100% is possible. The p-xylene feed can be supplied only to one reactor, or simultaneously to several reactors in any ratio. The oxygen feed and the p-xylene feed can also be fed into the reaction section as a combined feed. The temperatures and pressures of the feed streams may vary depending on the source of the feed and on the operation conditions of the reaction section to which it is fed.

The oxygen can be supplied in the same phase as the p-xylene, e.g., the liquid phase, or in the gaseous phase. For instance, oxygen may be provided to p-xylene by absorption of gaseous oxygen at elevated pressure through a selective membrane. Alternatively, oxygen may be absorbed into p-xylene by absorption out of an oxygen containing gas at high pressure, such as air or purified oxygen, and fed directly into the reactor and/or to a recycled stream from the reactor by diffusion through a selective membrane. Gaseous oxygen may be provided by evaporation or dissolution of liquid oxygen and absorption into a solvent, including supercritical fluids, and fed into the reactor medium from a saturated solution directly or indirectly depending on the characteristics of the oxygen-containing solvent. Oxygen may also be generated in situ by chemical reaction. Representative oxygen sources include, but are not limited to air, gaseous and liquid oxygen, hydrogen peroxide and the like.

The p-xylene solvent stream may include components other than the p-xylene and must typically be a liquid entering the reaction section. The p-xylene feed can contain components related to the process, e.g. unconverted reactants, products, co-products, intermediate products or side-products of the reaction or inert components.

The reaction occurs in the liquid phase in the presence of a solid catalyst, allowing selective conversion of p-xylene into TPA. The reaction conditions are maintained such that the TPA formed during the reaction remains in the liquid phase. Thus the concentration of the TPA solution is at least 0.5, 1, or 2 weight percent (wt %) or more and can range up to 5 or 10 wt % or more. In the conventional process, TPA precipitates during the reaction and generally has a very low solution concentration in the reaction medium. During TPA formation and precipitation, 4-CBA becomes trapped in the TPA crystals, leading to a crude product that requires further purification. By contrast, in the present process, the TPA produced during the reaction remains in the solution, and therefore 4-CBA is not trapped in the TPA produced. Instead, 4-CBA is converted into TPA. Hence, without further purification, the isolated TPA typically contains 0.1 wt % or less 4-CBA, 0.05 wt % or less 4-CBA, or even 0.01 or 0.005 wt % or less 4-CBA.

Solubility of TPA formed during the reaction is achieved by using p-xylene as solvent, optionally in combination with water, and maintaining reaction conditions suitable for increased solubility. In the presence of an easy to separate catalyst, such as an immobilized solid catalyst or a slurry catalyst, the water to p-xylene ratio, as well as the pressure and temperature, can be selected for sufficient TPA solubility, e.g., 0.1 to 50 mol % at the prevailing operating conditions. Typically, under adiabatic operating conditions, TPA solubility is selected to be 0.1 to 10 mol %.

Any catalyst for the oxidation of p-xylene which is in a heterogeneous (solid) phase versus the reaction medium can be used in the present invention. Suitable catalysts include encapsulated crystallites of 20 to 300 nm of catalytic principle in a mesoporous matrix. Cobalt-manganese compounds, especially those hosted in zeolites are particularly suitable.

For example, the catalyst having the following formula for the catalytic principle can be used: $CoMn_2(O)(R-COO)_6 L^1_{k1} L^2_{k2}$, wherein:
R is an optionally substituted $C_1$-$C_4$ alkyl;
$L^1$ is an optionally substituted nitrogen containing carboxylic acid;
$L^2$ is selected from the group consisting of $H_2O$, an optionally substituted $C_1$-$C_4$ alkyl containing carboxylic acid, an optionally substituted $C_5$-$C_6$ cycloalkyl or heterocycle, an optionally substituted $C_5$-$C_6$ heteroaryl or aryl;
k1+k2=3

Embodiments include catalysts of the above formula where R is —$CH_3$ or —$C_2H_5$; where $L^1$ is picolinic acid, nicotinic acid, or iso-nicotinic acid; and where $L^2$ is $CH_3COOH$ or $H_2O$.

Alternatively, catalysts may be employed with the catalytic principle having a formula corresponding to $CoMn_2(O)(R-COO)_{6-k3} L^3_{k3} L^4_{k4}$, wherein:
R is an optionally substituted $C_1$-$C_4$ alkyl;
$L^3$ is an optionally substituted nitrogen containing carboxylate;
$L^4$ is selected from the group consisting of $H_2O$, an optionally substituted nitrogen containing carboxylic acid, an optionally substituted $C_1$-$C_4$ alkyl containing carboxylic acid, an optionally substituted $C_5$-$C_6$ cycloalkyl or heterocycle, and an optionally substituted $C_5$-$C_6$ heteroaryl or aryl;
k3 is 1, 2, or 3;
k3+k4=3;

Embodiments include catalytic principles of the above formula where R is —$CH_3$ or —$C_2H_5$; where $L^3$ is 1-pyridine-COO$^-$, 2-pyridine-COO$^-$, or 3-pyridine-COO$^-$; and where $L^4$ is picolinic acid, nicotinic acid, i-nicotinic acid, $CH_3COOH$, or $H_2O$.

Catalytic principles presented herein have the metal complex hosted within a possibly functionally enhanced zeolite. Suitable zeolites are those which are able to contain the active principle either in cages of the zeolite or in a channel, preferably a crossing of two channels. Zeolites which are suitable for this are Faujasites (FAU), Hexagonal Faujasites (EMT) and beta (BEA) such as zeolite Y, zeolite X, zeolite LZ-210, SAPO-37, CSZ-1, EMC-2 but also including members of the associated disorder family, such as fibrous and the like, and micro-porous structures based on the above zeolites and mixtures thereof. Preferably use is made of a zeolite having an atomic Si/Al ratio of at least 8, as with these zeolites an optimal balance between porosity and diffusion characteristics are maintained.

For a detailed explanation of the structural similarities among zeolites and a list of references with specific structural information about zeolites, see, for example, U.S. Pat. Nos. 4,344,851; 4,503,023; 4,840,779; and Baerlocher et al., "Atlas of Zeolite Framework Types," ELSEVIER Fifth Revised Edition, (2001)). Preferred zeolites used to host the presented metal complexes include beta zeolite.

The mesoporous matrix comprises preferably mesoporous silica, carbon, carbon nanotubes and the like.

The phrase "alkyl" refers to hydrocarbyl groups comprising from 1 to 20 carbon atoms. The phrase "alkyl" includes straight chain alkyl groups such as methyl, ethyl, propyl, and the like. The phrase also includes branched chain isomers of straight chain alkyl groups. Additionally, alkyl groups can be optionally substituted according to the definition below. Thus, alkyl groups includes primary alkyl groups, secondary alkyl groups, and tertiary alkyl groups. Presently, preferred alkyl groups include unsubstituted alkyl groups having from 1 to 4 carbon atoms while even more preferred such groups have from 1 to 3 carbon atoms.

The phrase "substituted" refers to an atom or group of atoms that has been replaced with another substituent. The phrase "substituted" includes any level of substitution, i.e. mono-, di-, tri-, tetra-, or penta-substitution, where such substitution is chemically permissible. Substitutions can occur at any chemically accessible position and on any atom, such as substitution(s) on carbons. For example, substituted compound are those where one or more bonds to a hydrogen or carbon atom(s) contained therein are replaced by a bond to non-hydrogen and/or non-carbon atom(s).

The phrase "nitrogen containing carboxylic acid" refers to a compound comprising at least one carboxylic acid moiety (—COOH) and at least one optionally substituted nitrogen atom. Nitrogen containing carboxylic acid compounds embrace acyclic and cyclic structures, wherein the nitrogen can optionally be a ring member. For instance, nitrogen containing carboxylic acid encompass pyridines, picolines, pyrimidines, piperidines, and the like that comprise at least one —COOH. Preferable nitrogen containing carboxylic acids include picolinic acid, nicotinic acid, and i-nicotinic (the structures of which are shown below).

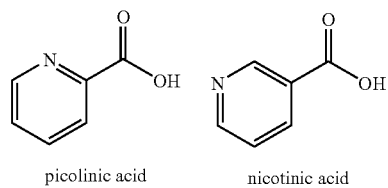

picolinic acid     nicotinic acid

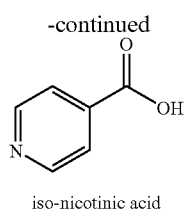

iso-nicotinic acid

The phrase "$C_1$-$C_4$ alkyl containing carboxylic acid" refers to a compound comprising at least one carboxylic acid moiety (—COOH) and at least one optionally substituted $C_1$-$C_4$ alkyl group. The phrase embraces straight chain, branched, and cyclic $C_1$-$C_4$ alkyl groups comprising at least one —COOH. Furthermore, the phrase also embraces $C_1$-$C_4$ alkyl groups containing any level of saturation. For instance, $C_1$-$C_4$ alkyl containing carboxylic acid compounds encompass acetic acid, propionic acid, butyric acid, and halogenated substitutions thereof, such as $CH_2FCOOH$, $CH_2ClCOOH$, $CH_2BrCOOH$, and the like. Preferable $C_1$-$C_4$ alkyl containing carboxylic acid include $CH_3COOH$.

The phrase "nitrogen containing carboxylate" refers to a compound comprising at least one carboxylate moiety (—COO$^-$) and at least one optionally substituted nitrogen atom. Nitrogen containing carboxylate compounds embrace acyclic and cyclic structures, wherein the nitrogen can optionally be a ring member. For instance, nitrogen containing carboxylates encompass pyridines, picolines, pyrimidines, piperidines, morpholine and the like that comprise at least one —COO$^-$. Preferable nitrogen containing carboxylates include 1-pyridine-COO$^-$, 2-pyridine-COO$^-$, and 3-pyridine-COO$^-$ (the structures of which are shown below).

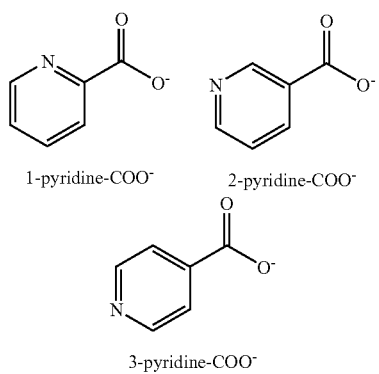

1-pyridine-COO$^-$    2-pyridine-COO$^-$ 3-pyridine-COO$^-$

The phrase "cycloalkyl" refers to a saturated or unsaturated alicyclic moiety having 1 to 20 carbon atoms. Cycloalkyl groups include cyclohexyl and cycloheptyl. The phrase "substituted cycloalkyl" refers to a cycloalkyl group that is substituted according to the definition provided above. Substituted cycloalkyl groups can have one or more atom substituted with straight or branched chain alkyl groups and can further comprise cycloalkyl groups that are substituted with other rings including fused rings. Representative substituted cycloalkyl groups may be mono-substituted such as, but not limited to 2-, 3-, 4-, 5-substituted cyclohexyl groups or mono-substituted groups, such as alkyl or halo groups.

The phrase "heterocycle" or "heterocyclic" refers to both aromatic and nonaromatic ring hydrocarbyl compounds. Heterocyclic groups include monocyclic, and bicyclic compounds containing 3 or more ring members of which one or more is a heteroatom such as, but not limited to, N and O. Examples of heterocyclyl groups include, but are not limited to, unsaturated 3 to 6 membered rings containing 1 to 3 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, and 2H-1,2,3-triazolyl); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 3 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, and 1,2,5-oxadiazolyl); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, and benzoxazinyl (e.g. 2H-1,4-benzoxazinyl). Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, and isoxazole. The phrase "substituted heterocycle" or "substituted heterocyclic" refers to a heterocyclic group that is substituted according to the definition provided above. Examples of substituted heterocyclic groups include, but are not limited to, 2-methylbenzimidazolyl, 5-methylbenzimidazolyl, 1-methyl piperazinyl, 2-chloropyridyl, and the like.

The phrase "aryl" refers to aromatic radicals comprising from 3 to 20 carbon atoms. Aryl groups include, but are not limited to, phenyl, biphenyl, anthracenyl, and naphthenyl. The phrase "substituted aryl group" refers to an aryl group that is substituted according to the definition provided above. For example, substituted aryl groups may be bonded to one or more carbon atom(s), oxygen atom(s), or nitrogen atom(s), and also includes aryl groups in which one or more aromatic carbons of the aryl group is bonded to a substituted and/or unsubstituted alkyl, alkenyl, or alkynyl group. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others. Preferably, aromatic groups are substituted with alkyl, carboxylic acid (—COOH), and/or carboxylate groups (—COO$^-$).

The phrase "heteroaryl" refers to a 3 to 20-membered aromatic ring consisting of carbon atoms and heteroatoms, such as N and O or (ii) an 8- to 10-membered bicyclic or polycyclic ring system consisting of carbon atoms and heteroatoms, such as N and O, wherein at least one of the rings in the bicyclic system is an aromatic ring. The heteroaryl ring may be attached at any heteroatom or carbon atom. Representative heteroaryl compounds include, for example, pyridyl, pyrazinyl, pyrimidinyl, pyridooxazolyl, pyridazooxazolyl, and pyrimidooxazolyl. The phrase "substituted heteroaryl" refers to a heteroaryl group that is substituted according to the definition provided above.

The reactor section includes one or more reactors in a series or parallel arrangement or any combination thereof. Each reactor can have a different level of mixing and temperature, and also different geometrical dimensions. The reaction section typically consists of a set of reactors in a series arrangement, where all reactors may or may not have similar mixing patterns and geometrical dimensions. The reaction takes place in the liquid phase, but a second phase or third phase, e.g. a liquid phase and/or a vapor phase, may be present. The catalyst can preferably be supplied as a slurry catalyst or as an immobilized solid catalyst. Other than the catalyst, no other solid phase should be present during the reaction. If a slurry catalyst is used, the catalyst recovery and recycle to the reactors is typically performed within the reactor section. Any method of catalyst separation can be applied, for example, restraining the solid catalyst from leaving the reactor by using wire mesh baskets, or using a catalyst separation device after each reactor, or performing catalyst recovery in a common device (e.g., a hydrocyclone) after the last reactor or any combination thereof. If the slurry catalyst separation is not an integral part of the reactor design any solid-liquid separation device that sufficiently separates the catalyst particles can be used.

Each reactor can be individually operated under adiabatic, isothermal, or non-adiabatic and non-isothermal conditions. Typically, the operating mode is adiabatic operation or isothermal operation using boiling cooling, e.g., by removing the heat of reaction or a part thereof by evaporating some of the reactor contents, subsequent condensation of the vapors in a cooling device and recycling the condensed liquid back to the reaction section. In a non-adiabatic and non-isothermal operation preferably only a part of the heat of reaction is removed, e.g. by boiling cooling, resulting in an increasing temperature profile in the reactor section with a lower temperature rise than the adiabatic case. The temperature and pressure in the reactors are strongly related to the water/p-xylene ratio used and the reactor setup and must be selected such that all the TPA formed during the reaction stays in the liquid phase. In the case of adiabatic operation, the reactor setup must also be selected to prevent evaporation of the reactor contents. Typical operating temperatures are in the range of from about 150° C. to about 400° C., and more typically from about 200° C. to about 300° C. Typical operating pressures are in the range of about 5 bar to about 80 bar, and in some embodiments, from about 30 bar to about 50 bar.

The reaction rate of oxidation methods presented herein is enhanced by the addition of a halogen containing agent. Representative halogen containing agents include hydrocarbyl brominating agents, such as 9-bromoanthracene, 9,10-dibromoanthracene and mixtures thereof. A halogen containing agent may be added to at least one reactor, or to multiple reactors within the reactor setup. In addition, the same or a different halogen containing agent may be added to each reactor within a series of reactors.

The effluent (C) from the reactor section is sent to the separation section, where the following tasks must be performed: TPA is separated, the water formed during the reaction is removed, and the p-xylene is recovered. The by-products can be removed, either in whole or in part, before the p-xylene and unconverted reactants are recycled. The tasks can occur in any sequence in the separation section. FIG. 1 shows a block diagram for an embodiment where water is removed first. Advantageously, water formed during the reaction is separated by a vapor-liquid based separation process. Typically the separation is performed in an adiabatic pressure flash by releasing the pressure of the reactor effluent, causing the most volatile components to evaporate and thus cooling down the remaining liquid. Pressure release can be performed either in a single step or multiple steps. During the water removal, other components such as the p-xylene will be present in the overhead vapor. Unreacted oxygen and other non-condensables will also be present. The vapor (E) is sent to the overhead system where water is removed after condensation (G). Evaporation and condensation can be performed in separate devices or a combined unit. Other valuable components such as unconverted p-xylene must be recovered and recycled back (F) to the main product stream. If any of the reactors are operated with boiling cooling, the off-gases (N) may also be treated in the overhead section. Non-condensable components will leave the system as an off-gas stream (H).

Partial evaporation of the contents of the reactor outlet combined with a drop in temperature will reduce the solubility of TPA in the liquid (D) and can cause precipitation of the TPA. If the TPA crystal yield is not sufficient, a subsequent crystallization step is required that may operate at a lower temperature, for instance. The final step in the illustrated TPA production route is a suitable solid-liquid separation unit, wherein the solid TPA (J) is separated from the liquid. Any solid-liquid separator that allows reliable separation of the solids from the liquid phase can be used (e.g., hydrocyclone or filtration). The liquid (K) discharged from the solid-liquid separation unit comprises p-xylene, water, non-recovered TPA, and non-volatile byproducts or intermediate products. Other streams in the process can be added before the p-xylene is recycled to the reactors. For example, TPA solubility in p-xylene can be improved by adding water. The p-xylene may be purified to prevent accumulation of trace components before recycling to the reactor section. Additional separation devices or purge streams can be used to remove the trace components (M).

Film-grade terephthalic acid is a grade of TPA that is suitable for making PET films. To this end, film-grade TPA is specified to contain extremely little or none of certain colored precursors. The most important colored precursor is 4-CBA, for which the specification is typically no more than 50 ppm.

Purified terephthalic acid (PTA) refers to film-grade terephthalic acid as obtained from a purification step, such as where 4-CBA in crude terephthalic acid is reduced by hydrogenation or some other treatment.

Adiabatic is a term referring to an operation where no heat is supplied to or withdrawn from that operation.

Isothermal is a term referring to an operation where the average temperature is the same in all parts of that operation. By average it is meant that small temperature fluctuations of, e.g., about 10% or less, may occur in confined parts of that operation.

Non-adiabatic is the antonym of adiabatic.

Non-isothermal is the antonym of isothermal.

Back-mixed is a term referring to an operation where the average composition is the same in all parts of that operation. By average it is meant that small fluctuations, e.g., about 20% or less, in composition may occur in confined parts of that operation. By contrast, partially backmixed systems will typically have a small concentration gradient between the inlet and outlet of the operation.

Reaction medium and reaction mixture both refer to the process mixture in which a chemical reaction takes place. For example, a reaction medium can include a solvent and one or more reactants.

Reaction solvent is the major constituent of a reaction medium. The reaction solvent serves to keep the reaction mixture in a specified condition, e.g., the solvent may keep the composition, the chemical and/or physical activity of components, and/or the temperature of the reaction at a particular value or range of values.

Co-solvent is a constituent of a solvent that serves a particular purpose, e.g. to maintain a certain solubility for TPA. A co-solvent may or may not take part in the chemical reaction.

A reaction section is the part of the flowsheet including all reactors. The reaction section usually includes all units in which chemical reactions take place, but may also include the unit(s) in which catalyst recycle occurs.

A separation section is the part of the flowsheet where an incoming mixture is separated into several fractions as required. For example, in the present methods, typical fractions are the product TPA, the p-xylene to recycle and by-products.

One skilled in the art will readily realize that all ranges discussed can and do necessarily also describe all subranges therein for all purposes and that all such subranges also form part and parcel of this invention. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

The present invention, thus generally described, will be understood more readily by reference to the following examples, which are provided by way of illustration and are not intended to be limiting of the present invention.

EXAMPLE

Figure 2:
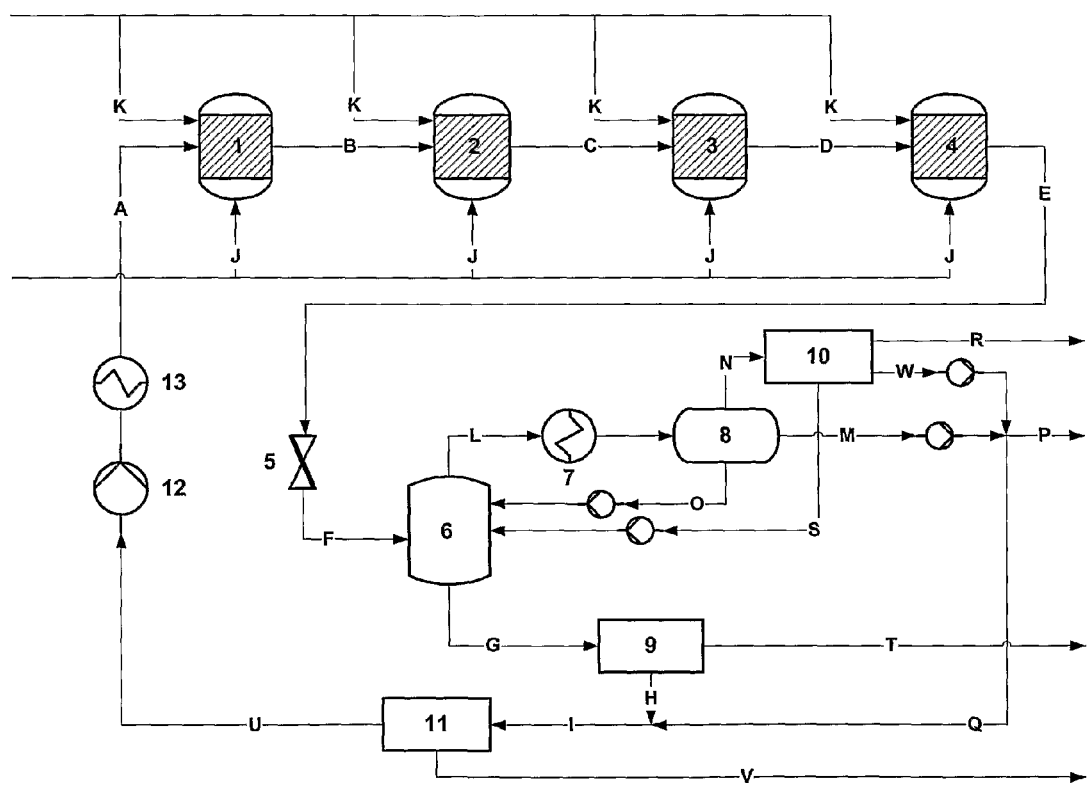
FIG. 2 shows a flow sheet for a process application using p-xylene as solvent.

A simplified flow sheet without any heat integration of a process according to the present invention with a p-xylene-water mixture used as solvent is shown in FIG. 2. The molar flow rates for the process in FIG. 2 are given in Table 1.

The main component of the solvent is p-xylene. A certain amount of water is mixed in as a TPA solubility enhancer. The reactor section includes four reactors shown by units 1, 2, 3, and 4, in FIG. 2. The reactors are operated in a series arrangement and include a solid immobilized catalyst. Each reactor is provided with a fresh p-xylene stream, K, and a fresh oxygen stream, J. The oxygen feed, J, consists of 95% of oxygen by volume, the rest being nitrogen, supplied at a reactor pressure of 50 bar absolute and at a temperature of 20° C. The p-xylene feed, K, consists of pure p-xylene, also at 50 bar absolute and 20° C. All the reactors are operated adiabatically and the reactor content is full liquid. Temperature levels in the reactors are 256° C. in reactor 1, 271° C. in reactor 2, 285° C. in reactor 3, and 300° C. in reactor 4. Total conversion of p-xylene is 1.5% and is equally distributed over all four reactors. The solvent is fed into the first reactor from the recycle loop stream A at a temperate of 240° C., consisting of 76.3 mol % p-xylene and 23.5 mol % water, the rest being dissolved TPA, by-products, reactants and inerts.

The effluent of reactor 4 is shown by stream E, at a temperature of 300° C. at 50 bar absolute and consists of 72.8 mol % p-xylene, 24.8 mol % water and 1.1 mol % TPA, the rest being side-products, oxygen and inerts. In the flash section the pressure of stream E is reduced to 16 bar absolute, and creates a vapor phase stream, L, which comprises 69.3 mol % p-xylene and 29.1 mol % water, the rest being by-products, reactants and inerts. In the heat exchanger shown by unit 7, stream E is cooled to 100° C. forcing condensation. The condensate splits into two immiscible liquid phases separated in unit 8 by decantation. The vapor phase stream, N, leaving unit 8 consists mainly of water and non-condensables and is sent to the off-gas treatment unit 10, where the gas is further purified. Components recovered from gas treatment are recycled as stream S back to the flash unit 6 and as stream W to the water outlet. The off-gas stream, R, is discharged from the process. The aqueous phase from units 8 and 10, consists primarily of water. The major part of the aqueous stream given by stream Q is added to the solvent loop to increase TPA

TABLE 1

| stream | | A | B | C | D | E | F | G | H |
|---|---|---|---|---|---|---|---|---|---|
| TPA | mol % | 0.06 | 0.33 | 0.60 | 0.86 | 1.11 | 1.11 | 1.35 | 0.07 |
| water | mol % | 23.47 | 23.82 | 24.15 | 24.48 | 24.80 | 24.80 | 10.37 | 10.50 |
| p-xylene | mol % | 76.27 | 75.38 | 74.51 | 73.66 | 72.83 | 72.83 | 88.08 | 89.22 |
| oxygen | mol % | 0.05 | 0.16 | 0.26 | 0.37 | 0.46 | 0.46 | 0.06 | 0.06 |
| others | mol % | 0.14 | 0.31 | 0.47 | 0.63 | 0.79 | 0.79 | 0.15 | 0.15 |
| pressure | bar | 50 | 50 | 50 | 50 | 50 | 16 | 16 | 16 |
| temperature | ° C. | 240 | 256 | 271 | 285 | 300 | 258 | 193 | 200 |
| total flow | kmol/h | 23841 | 24123 | 24406 | 24689 | 24971 | 24971 | 20647 | 20383 |

| stream | | I | J | K | L | M | N | O | P |
|---|---|---|---|---|---|---|---|---|---|
| TPA | mol % | 0.06 | 0.00 | 0.00 | 0.00 | 0.00 | 0.00 | 0.00 | 0.00 |
| water | mol % | 23.47 | 0.00 | 0.00 | 29.10 | 99.92 | 34.54 | 9.71 | 99.91 |
| p-xylene | mol % | 76.27 | 0.00 | 100.00 | 69.26 | 0.01 | 11.16 | 90.06 | 0.01 |
| oxygen | mol % | 0.05 | 95.00 | 0.00 | 0.61 | 0.01 | 20.76 | 0.07 | 0.01 |
| others | mol % | 0.14 | 5.00 | 0.00 | 1.03 | 0.06 | 33.54 | 0.17 | 0.07 |
| pressure | bar | 16 | 50 | 50 | 16 | 3 | 3 | 3 | 16 |
| temperature | ° C. | 176 | 20 | 20 | 258 | 100 | 100 | 100 | 101 |
| total flow | kmol/h | 23843 | 272 | 70 | 18702 | 3883 | 498 | 14321 | 594 |

| stream | | Q | R | S | T | U | V | W |
|---|---|---|---|---|---|---|---|---|
| TPA | mol % | 0.00 | 0.00 | 0.00 | 99.81 | 0.06 | 0.09 | 0.00 |
| water | mol % | 99.91 | 0.77 | 0.14 | 0.02 | 23.47 | 23.48 | 99.65 |
| p-xylene | mol % | 0.01 | 0.30 | 97.32 | 0.17 | 76.27 | 76.26 | 0.02 |
| oxygen | mol % | 0.01 | 38.05 | 0.22 | 0.00 | 0.05 | 0.09 | 0.01 |
| others | mol % | 0.07 | 60.88 | 2.32 | 0.00 | 0.14 | 0.09 | 0.32 |
| pressure | bar | 16 | 2 | 2 | 16 | 16 | 16 | 2 |
| temperature | ° C. | 101 | 15 | 15 | 200 | 176 | 176 | 15 |
| total flow | kmol/h | 3459 | 271 | 56 | 264 | 23842 | 1 | 170 | solubility. The rest, equal to the amount of water produced by the reaction, is discharged from the process and sent to waste water treatment as stream P. The organic phase from unit 8, is represented by stream O, and consists of more than 90 mol % of p-xylene. Stream O is recycled to the flash unit 6.

As a result of the evaporation of about a third of the p-xylene and almost two thirds of the water entering flash unit 6, the temperature therein drops below 200° C. Under these conditions the solubility of TPA in the liquid phase drops significantly, forcing about 95% of the TPA dissolved in the reactor effluent to precipitate. Stream G is withdrawn from flash unit 6, and comprises of a slurry with a solid content of about 2 wt %. The solid TPA, stream T, is separated from the slurry in the solid-liquid separation unit 9. Subsequent drying of the solid product to remove adhering mother-liquor is assumed to be outside boundary-limits of this process and therefore is not displayed in the figure. The remaining mother-liquor, stream H, is the major fraction of the solvent recycle. Together with a fraction of the water removed in units 8 and 10, it forms the solvent recycle I, which is sent to the solvent work-up section, 11, where the byproducts and other inerts are discharged to avoid accumulation. The outlet of the solvent workup is represented by stream U, which is pressurized, 12, and heated, 13, before entering the reactor section.

Figure 3A:
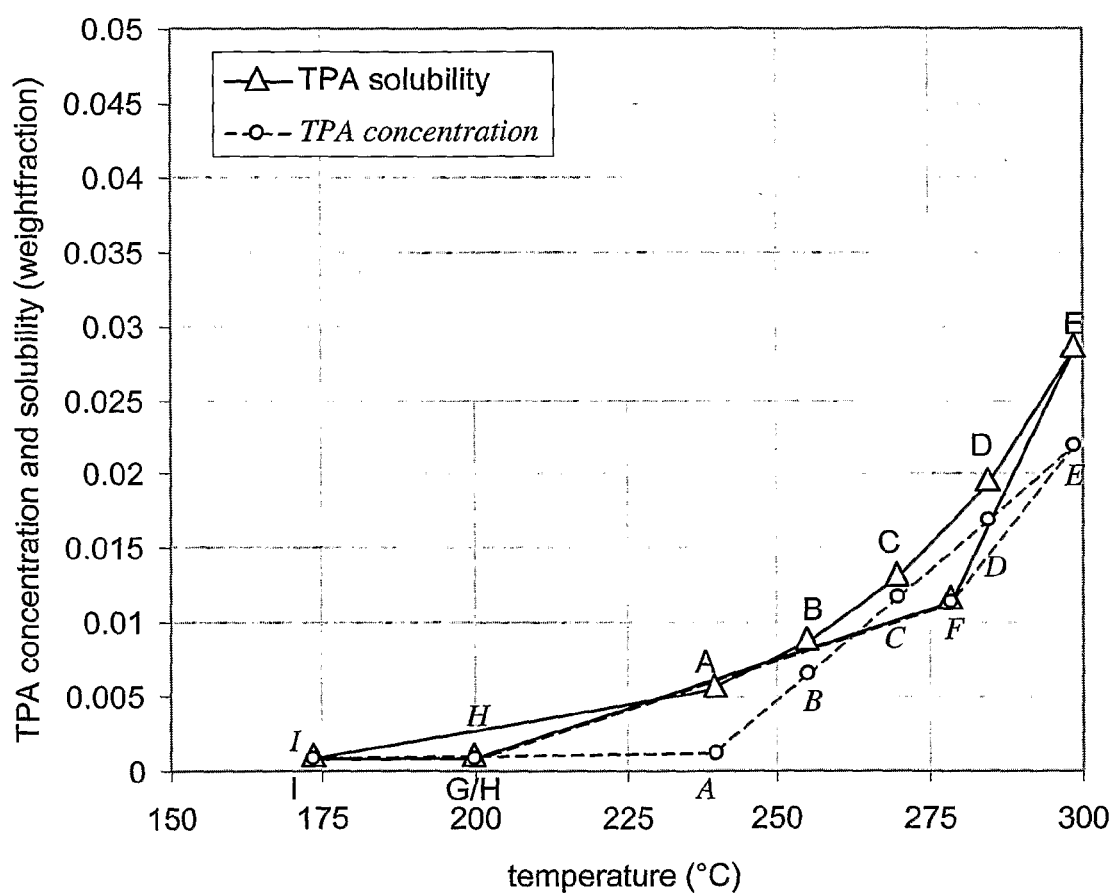
FIG. 3 shows the correlation between TPA solubility and TPA concentration in liquid phase as a function of the temperature (3A) and water concentration (3B).
Figure 3B:
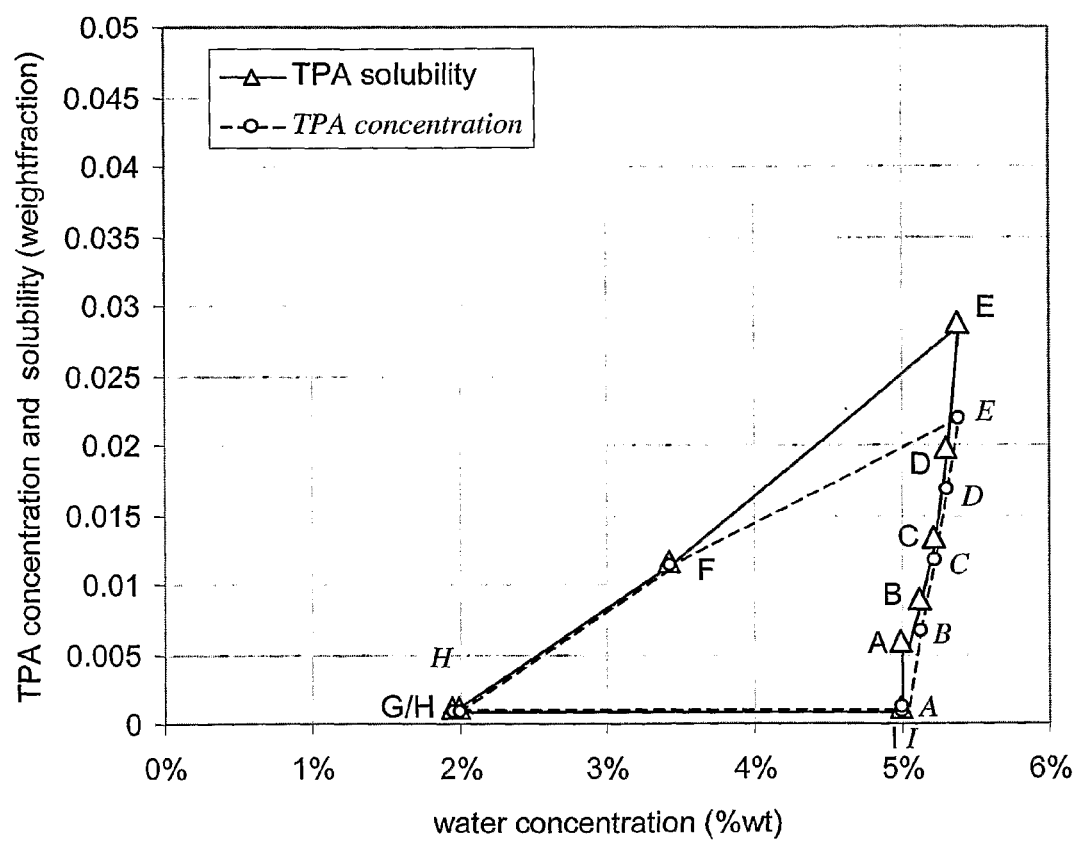

An important consequence of the process is that the TPA produced during the reaction stays in the liquid phase, thereby reducing the 4-CBA content in the TPA produced. A primary reason for the presence of 4-CBA impurity in the conventional process is that 4-CBA gets trapped in the TPA crystals due to structural similarity. The present invention avoids the precipitation of TPA during the reaction and thereby allows the 4-CBA to be converted to TPA. The process conditions are maintained such that TPA precipitates out only after leaving the reaction system, and the solvent recycled back to the reaction system is under-saturated in TPA. The TPA concentration and solubility profiles in the recycle loop are shown in FIG. 3 for varying temperatures (3A) and water concentrations (3B). The following describes the operations performed in going from one point to another in the solubility graphs.

A-E: Represents the reaction part of the process during which TPA is in the liquid phase. The adiabatic temperature rise over the reaction section is approximately 60° C. The overall conversion of p-xylene is kept low so that TPA does not precipitate during reaction, therefore, the water concentration does not increase significantly. The temperature increase during the reaction helps in increasing the solubility of TPA in p-xylene.

E-F: Adiabatic flashing due to pressure reduction drops the temperature by approximately 20° C. and the water concentration by approximately 2 wt %. This causes TPA to exceed the solubility limit sharply, leading to precipitation.

F-G: When the condensed and cooled p-xylene is mixed with the flash liquid, the temperature drops to 200° C. and causes the water concentration to fall by 1.5 wt % due to the dilution.

G-H: In the solid/liquid separator the TPA crystals are removed and the mother liquor is saturated in TPA. The solubility does not change in the separator and so G and H is the same point on the composition diagram.

H-I: Part of the condensed and cooled water is mixed with the mother liquor and as a result the solubility of TPA increases.

I-A: The recycle stream is heated to 240° C. before it enters the reaction section. The rise in temperature increases the TPA solubility as shown in FIG. 5. The increase in pressure does not have a significant impact on the solubility.

The invention claimed is:

1. A method comprising reacting a starting material and oxygen in the presence of a heterogeneous catalyst and p-xylene, and optionally water, as solvent to produce a solution of terephthalic acid without formation of solid terephthalic acid during the reaction, wherein the starting material is p-xylene, p-toluic acid, 4-carboxybenzaldehyde, or a mixture of two or more thereof, and wherein if water is present, the ratio of water to xylene is from about 0.01 to about 1 by weight.

2. The method of claim 1 wherein the oxygen is supplied from a gas comprising at least 18% oxygen by volume.

3. The method of claim 1 wherein the oxygen is supplied from a gas comprising at least 90% oxygen by volume.

4. The method of claim 1 wherein the catalyst is a solid catalyst.

5. The method of claim 4 wherein the solid catalyst is immobilized on a substrate or is a slurry catalyst.

6. The method of claim 4 wherein the solid catalyst comprises an inert mesoporous encapsulating matrix.

7. The method of claim 4 wherein the solid catalyst comprises a cobalt manganese compound.

8. The method of claim 1 wherein the starting material and oxygen are reacted in the presence of a halogen-containing agent.

9. The method of claim 1 wherein the p-xylene solvent further contains water as co-solvent.

10. The method of claim 9 wherein the solvent is a mixture of p-xylene and water, in a water to p-xylene weight ratio of between 0.01 and 1.

11. The method of claim 1 wherein the reaction of p-xylene and oxygen is carried out at temperature of about 150° C. to about 400° C.

12. The method of claim 1 wherein the reaction of p-xylene and oxygen is carried out at a pressure of about 5 bar to about 80 bar.

13. The method of claim 9 wherein at least a portion of the water separated is recycled for use as co-solvent.

14. The method of claim 1 wherein the reaction medium comprises oxygen, p-xylene, water and terephthalic acid as a single homogeneous liquid phase.

15. The method of claim 1 further comprising separating terephthalic acid from the solution of terephthalic acid.

16. The method of claim 15 wherein the separation is carried out by flash evaporation of water from the solution of terephthalic acid.

17. The method of claim 1 further comprising separating water from the reaction mixture or the solution of terephthalic acid.

18. The method of claim 1 wherein the water is separated by pressure flashing, subsequent liquid-liquid separation of the condensed vapors, and recycling of the p-xylene phase.

19. The method of claim 10 wherein:
the reaction of p-xylene and oxygen is carried out at temperature of about 150° C. to about 400° C.;
the reaction of p-xylene and oxygen is carried out at a pressure of about 5 bar to about 80 bar;
the p-xylene solvent further contains water as co-solvent;
at least a portion of the water separated is recycled for use as co-solvent;
the reaction medium comprises oxygen, p-xylene, water and terephthalic acid as a single homogeneous liquid phase;
terephthalic acid is separated from the solution of terephthalic acid;

the separation is carried out by flash evaporation of water from the solution of terephthalic acid;

water is separated from the reaction mixture or the solution of terephthalic acid;

the water is separated by pressure flashing, subsequent liquid-liquid separation of the condensed vapors, and recycling of the p-xylene phase.

20. The method of claim 15 wherein separation of terephthalic acid is by precipitation, crystallization, or both precipitation and crystallization.

21. The method of claim 4 wherein the solid catalyst comprises an inert mesoporous encapsulating matrix as mesoporous $SiO_2$ or carbon.

22. The method of claim 4, wherein the catalyst is based on a zeolite.

23. The method of claim 8, wherein the halogen-containing agent is 9-bromoanthracene, 9,10-dibromoanthracene, or a mixture thereof.

* * * * *